(12) United States Patent
Renard et al.

(10) Patent No.: US 9,211,242 B2
(45) Date of Patent: Dec. 15, 2015

(54) NAIL-HARDENING COSMETIC COMPOSITION, USE OF ALDEHYDES TO HARDEN AND STRENGTHEN NAILS, AND METHOD FOR APPLYING SAME

(71) Applicant: FIABILA, Maintenon (FR)

(72) Inventors: Christine Renard, Maintenon (FR); Xavier Bonnevie, Mainvilliers (FR)

(73) Assignee: FIABILA, Maintenon (FR)

( * ) Notice: Subject to any disclaimer, the term of this patent is extended or adjusted under 35 U.S.C. 154(b) by 0 days.

(21) Appl. No.: 14/275,909

(22) Filed: May 13, 2014

(65) Prior Publication Data

US 2014/0248225 A1   Sep. 4, 2014

Related U.S. Application Data

(62) Division of application No. 13/257,081, filed as application No. PCT/FR2010/050579 on Mar. 30, 2010, now abandoned.

(30) Foreign Application Priority Data

Mar. 30, 2009   (FR) ..................... 09 01522

(51) Int. Cl.
*A61K 8/33* (2006.01)
*A61Q 3/00* (2006.01)
*A61Q 3/02* (2006.01)

(52) U.S. Cl.
CPC ... *A61K 8/33* (2013.01); *A61Q 3/00* (2013.01); *A61Q 3/02* (2013.01)

(58) Field of Classification Search
None
See application file for complete search history.

(56) References Cited

U.S. PATENT DOCUMENTS

| 4,919,920 | A | 4/1990 | Devos |
| 2002/0192247 | A1 | 12/2002 | Theisen |
| 2003/0124154 | A1 | 7/2003 | Amato et al. |
| 2004/0170584 | A1 | 9/2004 | Renard |

FOREIGN PATENT DOCUMENTS

| EP | 1238650 | 9/2002 |
| EP | 1336346 | 8/2003 |
| EP | 1408917 | 9/2006 |
| GB | 1183513 | 3/1970 |
| GB | 2196978 | 5/1988 |
| GB | 2250196 | 6/1992 |
| WO | 9107942 | 6/1991 |
| WO | 0139739 | 6/2001 |
| WO | 03005975 | 1/2003 |
| WO | 2008138547 | 11/2008 |

OTHER PUBLICATIONS

International Search Report dated Jul. 19, 2011, from corresponding PCT application.

*Primary Examiner* — Bethany Barham
*Assistant Examiner* — Barbara Frazier
(74) *Attorney, Agent, or Firm* — Young & Thompson

(57) ABSTRACT

A cosmetic composition for nails containing a concentration less than or equal to 1 wt % of at least one monoaldehyde of the formula (I): R—CHO, where R is C5-C12 linear alkyl radical or a C5-C12 alkenyl with an unconjugated double bond to the —CHO aldehyde group, as nail hardening agent, and provided in the form of a colored or colorless fingernail polish, a polish undercoat, a peelable polish, a beauty oil, an emulsion or an aqueous solution, or a gel. Also the use of aldehydes of the formula (I) for hardening and strengthening nails and to a method for applying same.

5 Claims, No Drawings

NAIL-HARDENING COSMETIC COMPOSITION, USE OF ALDEHYDES TO HARDEN AND STRENGTHEN NAILS, AND METHOD FOR APPLYING SAME

The invention relates to the field of cosmetic compositions for nails, and more particularly cosmetic compositions for strengthening and hardening nails.

It is well known that nails, which are composed of keratin, are sometimes weakened, brittle, split or cracked. Besides degrading the esthetic appearance of these nails, this results in considerable inconvenience for a person in their daily life, mainly when these defects relate to fingernails: catching on textiles or clothing, aggravating cracks each time something is gripped, etc.

To date, various solutions have been provided for this problem, but the latter are either not perfect, or generate other drawbacks. Mention may thus be made of the following:

The use of formaldehyde, in proportions that may range up to 5% by weight in the cosmetic composition, has been known for a long time. However, this compound is now monitored very closely due to its toxic effects on the body, with proven carcinogenic effects. This molecule is moreover a powerful allergen.

The use of glyoxal, a dialdehyde, was described in patent GB 2 196 978 as early as 1986. This product is however harmful by inhalation, irritating to the skin and the eyes, and may cause skin sensitization.

The use of glutaraldehyde is described in patent GB 2 250 196 in combination with a water-soluble aluminum salt for hardening horses' hooves, which are also composed of keratin. However, it turns out that this aldehyde is toxic by inhalation and if swallowed, may cause burns, and may cause sensitization by skin contact: it therefore appears quite unsuitable for human nails.

Patent GB 1 183 513 indicates that the hardening action of aldehydes on the nails decreases mitten the number of carbon atoms increases. It recommends the use of $C_1$ to $C_4$ monoaldehydes, more particularly acetaldehyde, or dialdehydes for strengthening the keratin of the nails, at contents between 3% and 5%.

Citral (in the form of a mixture of its two isomers geranial and neral), described in patent EP 1 408 917, is certainly also recognized for its nail-hardening action, but may cause sensitization by skin contact and is classed among the detected allergens according to the list of allergenic substances cited in the 7th amendment of European Directive 76/768/EEC). It is therefore used less and less in cosmetics. Moreover, these molecules comprise a double bond, which makes citral UV-sensitive, and therefore subject to yellowing.

This long list of drawbacks relating to the aldehydes used in cosmetic compositions for nails has encouraged those skilled in the art to research other types of non-aldehyde molecules for hardening and strengthening human nails.

Among the other nail hardeners, document U.S. Pat. No. 4,919,920 describes the incorporation of iodine or fluorine in the form of ions in an aqueous cosmetic composition with no organic solvent, optionally in the presence of a polyol such as glycerol. Such a use is not suitable for nail polishes that comprise a large organic solvent phase. Iodine may also cause allergies in certain users.

There remains therefore a real need to find a compound for hardening nails that overcomes the aforementioned drawbacks and that can be used in diverse cosmetic compositions, that is to say cosmetic compositions of different natures, namely polish, gels or care oils for example.

A first objective of the invention is therefore to propose the implementation and use of a family of compounds for strengthening the keratin structure of the nail by hardening it, which does not have the drawbacks mentioned above.

Another objective of the invention is to propose compounds that are not sensitive to aging, and especially to yellowing.

Yet another objective of the invention is to propose a compound for hardening nails that does not have an odor that is unpleasant for the user, at concentrations below a few percent by weight.

For this purpose, the present invention proposes the use, as a nail hardening agent, of a monoaldehyde of formula (I): R—CHO, R being a linear $C_5$-$C_{12}$ alkyl radical, or a $C_5$-$C_{12}$ alkenyl having a double bond that is not conjugated with the —CHO aldehyde group, preferably not belonging to the list of allergenic substances cited in the 7th amendment of European Directive 76/768/EEC.

Indeed, it has been observed, surprisingly and contrary to the indications from the prior art (in particular from patent GB 1 183 513) that monoaldehydes having alkyl or alkenyl radicals comprising from 5 to 12 carbon atoms exhibit nail-hardening properties.

Moreover, these aldehydes do not exhibit yellowing over time and do not have an odor that is unpleasant for the user, at concentrations less than or equal to 1% by weight. Thus, the aldehyde of formula (I) can be used in a cosmetic composition for nails.

Advantageously, said cosmetic composition contains a concentration of aldehyde of formula (I) of less than or equal to 1% by weight, preferably less than or equal to 0.5% by weight. More advantageously, the cosmetic composition contains a concentration of aldehyde of formula (I) of less than or equal to 0.1% by weight, preferably less than or equal to 0.05% by weight.

It has also been observed, that the nail-hardening properties are present even at concentrations of less than or equal to 0.01% by weight of aldehyde of formula (I).

The aldehyde of formula (I) may advantageously be chosen from hexanal, heptanal, octanal, nonanal, dodecanal, trans-4-decenal, undecanal and undecylenic aldehyde, or a mixture thereof.

These aldehydes have the advantage of not presenting any health risk (sensitization, allergy, toxicity, nor carcinogenic effect, unlike certain active agents from the prior art).

For example, surprisingly, hexanal, which is used in the agri-food sector in particular for flavoring beverages, has proved to be active as a nail hardener. Hexanal, which may be derived from enzymatic treatments of sunflower oil, is already known as a natural flavoring substance.

According to the present invention, the aldehyde of formula (I) may be incorporated into a cosmetic composition which may be a film-forming composition, such as a colored or colorless nail polish, a polish base coat or a peelable polish, or may be in the form of an aqueous solution or emulsion, a care oil, or a gel. Film-forming cosmetic compositions, such as polishes, are preferred since they can remain on the nail in a lasting manner.

The present invention also relates to any cosmetic composition for the nails, containing a concentration of less than or equal to 1% by weight of at least one monoaldehyde of formula (I) as a nail hardening agent, and preferably being in the form of a colored or colorless nail polish, a polish base coat, a peelable polish, a care oil, an aqueous solution or emulsion, or a gel.

Studies of the efficacy of said compositions show that these aldehydes are active on several levels with respect to nail defects: cracked nails, thin nails, brittle nails, split nails, hardness of the nail, weakness of the nail, without causing allergic reactions.

The present invention also relates to a process for hardening the nails, especially cracked, thin, brittle, soft or split nails, consisting in applying topically to said nails and/or the periphery thereof, a monoaldehyde of formula (I): R—CHO, R being a linear $C_5$-$C_{12}$ alkyl radical, or a $C_5$-$C_{12}$ alkenyl having a double bond that is not conjugated with the —CHO aldehyde group. The aldehyde of formula (I) is advantageously present in a cosmetic composition for nails, it being possible for this cosmetic composition to be in particular in the form of a colored or colorless nail polish, a polish base coat, a peelable polish, a care oil, an aqueous solution or emulsion, or a gel.

The following examples make it possible to illustrate the present invention in a non-limiting manner. In all of the formulations, the concentration of the various constituents is expressed as % by weight of the total weight of the cosmetic composition.

EXAMPLE 1

A cosmetic composition in the form of a thixotropic polish was prepared from the following constituents:

| | |
|---|---|
| Butyl acetate | 41.00 |
| Ethyl acetate | 20.60 |
| Nitrocellulose | 14.00 |
| Polyester resin | 9.50 |
| Acetyl tributyl citrate | 6.00 |
| Isopropyl alcohol | 6.00 |
| Stearalkonium bentonite | 1.30 |
| Styrene/acrylic resin | 1.30 |
| Benzophenone-1 | 0.20 |
| Polyvinyl butyral | 0.05 |
| Hexanal | 0.05 |
| | 100.00 |

This composition is here in the form of a polish, which is colorless and transparent after application to the nail, having a solids content equal to 31.3% by weight (measured at 100° C.). One or more dyestuffs chosen from pigments, soluble dyes and decorative particles, such as nacres and flakes, may be added.

Physical Characteristics:

The following were tested:
  The gloss: 87 (on a scale of 100). It is measured with a Minolta 268 glossmeter (angle of incidence 60°) for an application made on a LENETA type card.
  The hardness, measured using a "Persoz" pendulum on the dry film formed by applying a 100 μm thick layer of the above composition onto a glass plate, dried overnight at room temperature (20° C.), the value obtained is 210 seconds.
  Good adhesion to glass with a value between 0 and 1 (on a scale of 5). The film of polish formed on glass is scratched in a crosshatched manner with a six-blade comb of SHEEN 750/1 type. An adhesive tape applied over the scratches is torn off, and it is observed that less than 5% of the surface of the film is torn off.
  The viscosities, measured using a Brookfield LVT viscometer with a No. 3 spindle at 25° C. at 6 rpm and at 60 rpm for one minute, had the following values: (in mPa·s, respectively at 6 rpm-60 rpm-6 rpm) 2400-960-1350. This corresponds to a good spreadability of the polish.

Hexanal, at this concentration, does not have an odor that is unpleasant for the user.

In Vivo Tests:

The composition from example 1 was the subject of in vivo tests on a panel of 22 people aged at least 30 years old, over four weeks, in order to evaluate the efficacy and tolerance. None of the people tested had a lesion in the vicinity of the target zones (here the periphery of the fingernails), nor a dermatological condition. The polish was applied under normal usage conditions (namely three applications per week). These results are presented in the table below:

TABLE 1

Number of subjects having observed an improvement (number of subjects tested: 22)

| Improvement | Slight | Moderate | Substantial | Very substantial | Total |
|---|---|---|---|---|---|
| Nail weakness | 6 | 7 | 2 | 3 | 18/22 = 82% |
| Cracked nail | 7 | 1 | 0 | 1 | 9/14 = 64% |
| Thin nail | 8 | 2 | 4 | 2 | 16/22 = 73% |
| Relief of the nail plate | 7 | 1 | 3 | 0 | 11/22 = 50% |
| Brittle nail | 5 | 3 | 4 | 3 | 15/22 = 68% |
| Split nail | 5 | 4 | 3 | 2 | 14/20 = 70% |
| Nail hardness | 3 | 5 | 5 | 5 | 18/22 = 82% |
| Overall improvement in nail quality | 3 | 3 | 9 | 5 | 20/22 = 91% |
| Tolerance to the product | Good for all subjects | | | | |

The tolerance was evaluated 30 minutes after application and at the end of the four-week test. No clinical signs of intolerance were observed, nor experienced by the people tested. No allergy symptoms were observed.

Moreover, more than 90% of subjects noticed an overall improvement in the quality of their nails. These results demonstrate the in vivo nail-hardening properties of hexanal, at low concentration (0.05% by weight).

Furthermore, the overall cosmetic qualities of the composition received a very favorable assessment (average marks between 16 and 17/20).

EXAMPLE 2

In vivo Tests/Comparison with a Dialdehyde from the Prior Art (Citral Described in Patent Application EP 1 408 917 Cited in the Introduction):

The composition of example 1 and also a composition 1a identical to that of example 1, but in which the hexanal has been replaced by citral, in the same concentrations, were the subject of in vivo tests on a new panel of 22 people under the same conditions as those of the tests from example 1. Each person applied the composition with hexanal to the nails of one hand, and the composition with citral to the nails of the other hand. The right hand/left hand choice was random.

The results of the comparative tests show that hexanal is between 8% and 20% superior to citral from the point of view of the improvement in:
  nail weakness (+18%)
  brittle nails (+10%)
  nail hardness (+8.5%).

Hexanal is therefore more suitable for strengthening the nail than citral.

EXAMPLE 3

A cosmetic composition in the form of a thixotropic polish identical to the composition of example 1, replacing the hexanal with dodecanal.

The results of the in vivo tests performed on a panel of 21 people under the same conditions as the tests from example 1 showed that more than half the subjects observed an overall improvement in the condition of their nails, especially as regards nail weakness, thin nails, brittle nails, and nail hardness. The marks of general satisfaction with the cosmetic composition oscillated between 16.9 and 18.3/20.

EXAMPLE 4

A cosmetic composition in the form of a thixotropic polish identical to the composition of example 1, replacing the hexanal with undecylenic aldehyde (10-undecenal).

The results of the in vivo tests performed on a panel of 21 people under the same conditions as the tests from example 1 showed that more than half the subjects observed an overall improvement in the condition of their nails, especially as regards nail weakness, thin nails, split nails, and nail hardness. The marks of general satisfaction with the cosmetic composition oscillated between 16 and 17.3/20.

EXAMPLE 5

The colored, transparent, film-forming composition, in which the proportion of hexanal is 0.20%, comprises the following constituents:

| | |
|---|---|
| Ethyl acetate | 40.00 |
| Butyl acetate | 26.5796 |
| Nitrocellulose | 14.00 |
| Polyester resin | 7.00 |
| Acetyl tributyl citrate | 6.20 |
| Isopropyl alcohol | 6.00 |
| Hexanal | 0.20 |
| Polyvinyl butyral | 0.02 |
| Red 17 | 0.0002 |
| Violet 2 | 0.0002 |

EXAMPLE 6

Hexanal is incorporated into a care oil for strengthening the nail, having the following formulation:

| | |
|---|---|
| Sweet almond oil | 98.99 |
| Fragrance | 1.00 |
| Hexanal | 0.01 |

EXAMPLE 7

In this example, the hexanal is incorporated into a care gel, also at a concentration of 0.01% by weight.

| | |
|---|---|
| Water | 83.59 |
| Glycerol | 5.00 |
| Propylene glycol | 5.00 |
| Trisodium phosphate | 3.80 |
| Carbomer | 0.90 |
| Laureth 4 | 0.80 |
| Phenonip ® | 0.70 |
| Fragrance | 0.20 |
| Hexanal | 0.01 |

Phenonip® is a trademarked preservative product from the company Nipa that contains a mixture of paraben in solution in phenoxyethanol.

EXAMPLE 8

Hexanal may also be effective in an aqueous-based care polish, constituted of:

| | |
|---|---|
| Water | 54.80 |
| Polyvinyl acetate | 40.00 |
| PPG 3 methyl ether | 3.00 |
| Ammonium citrate | 0.60 |
| Titanium oxide | 0.55 |
| Phenonip ® | 0.50 |
| PEG 12 dimethicone | 0.30 |
| Styrene/acrylic copolymer | 0.15 |
| DC Red 30 | 0.05 |
| Hexanal | 0.05 |

This polish adheres weakly to the nail and is detached from the nail by peeling (peelable polish). It may be used as an overnight care product.

The various examples above showed that hexanal may be incorporated into cosmetic compositions of different natures [all the above cosmetic compositions including hexanal at low concentrations, here less than or equal to 0.05% by weight] and that it has a strengthening and hardening effect on the nails.

EXAMPLE 9

Aging and Yellowing Tests

Various aliphatic aldehydes were incorporated into a cosmetic composition, having a formulation corresponding to example 2, at concentrations respectively of 0.001%, 0.002%, 0.005% and 0.01%.

These were methylbutyraldehyde (by way of comparison), hexanal, nonanal, trans-4-decenal, undecanal and undecylenic aldehyde.

The aging, and in particular the tendency toward yellowing, of each composition were tested. The various tests performed comprise holding for one month in an oven at 45° C. and four months in an oven at 50° C., and also exposure to "SUNTEST CPS+", i.e. in a sealed chamber, regulated at 50° C. under a 500 Watt/m$^2$ UV/visible lamp for 3×10 hours.

The yellowing was evaluated relative to control compositions having identical formulations, kept at room temperature (20-25° C.), in the dark, for the same duration.

All the polishes tested remained fluid over time and were spread easily and in the same way as the controls.

The compositions containing concentrations of 0.01% of methylbutyraldehyde or of undecylenic aldehyde exhibited yellowing after one month in an oven at 45° C.

Hexanal, nonanal, trans-4-decenal and undecanal did not exhibit yellowing at the same concentrations (0.01% by weight).

The invention claimed is:
1. A process for hardening the nails comprising:
applying topically to said nails and/or the periphery thereof, a monoaldehyde of formula (I): R—CHO, R being a linear $C_5$-$C_{12}$ alkyl radical, or a $C_5$-$C_{12}$ alkenyl having a double bond that is not conjugated with the —CHO aldehyde group,
wherein said aldehyde of formula (I) is present in a cosmetic composition for nails at a concentration less than or equal to 1% by weight of the cosmetic composition.
2. The process as claimed in claim 1, wherein the cosmetic composition is in the form of a colored or colorless nail polish, a polish base coat, a peelable polish, a care oil, an aqueous solution or emulsion, or a gel.

3. The process as claimed in claim 1, wherein the monoaldehyde of formula (I) is less than or equal to 0.1% by weight of the cosmetic composition.

4. The process as claimed in claim 1, wherein the aldehyde of formula (I) is selected from the group consisting of hexanal, heptanal, octanal, nonanal, dodecanal, trans-4-decenal, undecanal and undecylenic aldehyde, and a mixture thereof.

5. The process as claimed in claim 1, wherein the nails are cracked, thin, brittle, soft or split nails.

\* \* \* \* \*